US009840361B2

(12) United States Patent
Gordon et al.

(10) Patent No.: US 9,840,361 B2
(45) Date of Patent: Dec. 12, 2017

(54) GAS CELL DRIVEN ORIENTATION INDEPENDENT DELIVERY DEVICE

(71) Applicant: Microlin, LLC, Salt Lake City, UT (US)

(72) Inventors: John Howard Gordon, Salt Lake City, UT (US); Ashok V. Joshi, Salt Lake City, UT (US)

(73) Assignee: Microlin, LLC, Salt Lake City, UT (US)

( * ) Notice: Subject to any disclaimer, the term of this patent is extended or adjusted under 35 U.S.C. 154(b) by 496 days.

(21) Appl. No.: 14/010,242

(22) Filed: Aug. 26, 2013

(65) Prior Publication Data

US 2014/0057174 A1 Feb. 27, 2014

Related U.S. Application Data

(60) Provisional application No. 61/692,750, filed on Aug. 24, 2012.

(51) Int. Cl.
*A61M 5/145* (2006.01)
*B65D 83/00* (2006.01)
(Continued)

(52) U.S. Cl.
CPC ....... *B65D 83/0072* (2013.01); *A61M 5/1483* (2013.01); *A61M 5/14593* (2013.01); *A61M 5/155* (2013.01); *B05B 9/047* (2013.01); *B05B 11/0043* (2013.01); *B05B 11/0059* (2013.01); *B05B 11/02* (2013.01); *B05B 11/046* (2013.01); *B05B 11/3028* (2013.01); *A61M 2005/14204* (2013.01); *C25B 9/06* (2013.01);
(Continued)

(58) Field of Classification Search
CPC ........ A61M 2005/14204; A61M 5/155; A61M 5/1483; F16N 11/10; B67D 7/72
See application file for complete search history.

(56) References Cited

U.S. PATENT DOCUMENTS 3,471,349 A 10/1969 Cohen
3,504,827 A * 4/1970 Larson ................... B64D 37/06
222/136
(Continued)

OTHER PUBLICATIONS

Permeability Coefficients of Common Polymers—Reference Sheet.*

(Continued)

*Primary Examiner* — Alexander Valvis
(74) *Attorney, Agent, or Firm* — Brian C. Trask

(57) ABSTRACT

An orientation independent delivery device. The delivery device includes a gas chamber, a delivery chamber, a gas cell, and a delivery aperture. The gas chamber includes a gas-side rigid portion and a gas-side flexible barrier. The gas-side flexible barrier is sealed to the gas-side rigid portion. The delivery chamber includes a delivery-side rigid portion and a delivery-side flexible barrier. The delivery-side flexible barrier is sealed to the delivery-side rigid portion and is oriented adjacent to the gas-side flexible barrier. The gas cell is coupled to the gas-side rigid portion of the gas chamber. The gas cell increases a gas pressure within the gas chamber to expand the gas-side flexible barrier. Expansion of the gas-side flexible barrier applies a compressive force to the delivery-side flexible barrier allowing a delivery material to escape from the delivery chamber.

14 Claims, 6 Drawing Sheets

(51) Int. Cl.
*A61M 5/148* (2006.01)
*A61M 5/155* (2006.01)
*B05B 9/047* (2006.01)
*B05B 11/00* (2006.01)
*B05B 11/02* (2006.01)
*B05B 11/04* (2006.01)
*A61M 5/142* (2006.01)
*C25B 9/06* (2006.01)

(52) U.S. Cl.
CPC ............... *F17C 2201/0142* (2013.01); *F17C 2201/0147* (2013.01); *F17C 2201/0176* (2013.01); *F17C 2203/066* (2013.01); *F17C 2203/0685* (2013.01)

(56) References Cited

U.S. PATENT DOCUMENTS

| | | | |
|---|---|---|---|
| 3,940,032 A | | 2/1976 | Gershon |
| 3,945,539 A | | 3/1976 | Sossong |
| 4,358,026 A | | 11/1982 | Makinen |
| 5,090,963 A | * | 2/1992 | Gross .................. A61M 5/155 128/DIG. 12 |
| 5,399,166 A | * | 3/1995 | Laing .................. A61M 5/1483 604/131 |
| 5,573,646 A | | 11/1996 | Saito et al. |
| 5,738,657 A | * | 4/1998 | Bryant .................. B01J 7/02 222/95 |
| 5,744,014 A | | 4/1998 | Gordon et al. |
| 5,785,688 A | * | 7/1998 | Joshi .................. A61M 5/14593 604/132 |
| 5,899,381 A | | 5/1999 | Gordon et al. |
| 2012/0060947 A1 | * | 3/2012 | Reichert .................. A45F 3/20 137/565.01 |
| 2013/0095225 A1 | * | 4/2013 | Lebaron .................. A23L 3/0155 426/665 |

OTHER PUBLICATIONS

Extended European Search Report, dated Mar. 31, 2016.
Ahn, Yae Y., "International Search Report", PCT Application No. PCT/US2013/056662 (Corresponding to U.S. Appl. No. 14/010,242), (dated Nov. 25, 2013),1-3.
Ahn, Jae Y., "Written Opinion of the International Searching Authority", PCT Application No. PCT/US2013/056662 (Corresponding to U.S. Appl. No. 14/010,242), (dated Nov. 25, 2013),1-8.

* cited by examiner

GAS CELL DRIVEN ORIENTATION INDEPENDENT DELIVERY DEVICE

CROSS-REFERENCE TO RELATED APPLICATIONS

This application claims the benefit of U.S. Provisional Application No. 61/692,750, filed on Aug. 24, 2012, which is incorporated by reference herein in its entirety.

BACKGROUND

Liquid and gas delivery systems serve many roles in many different fields from medical treatment devices to air fresheners. Frequently, conventional delivery systems involve some variety of a pump. Many different types of pumps exist with different strengths and weaknesses.

For example, some pumps are orientation sensitive. These pumps must be aligned or situated within certain thresholds to function properly. Other pumps require large amounts of operating force to move small amounts of material. Some pumps are susceptible to debris and particulate matter within a fluid stream.

SUMMARY

Embodiments of a device are described. In one embodiment, the device is an orientation independent delivery device. The delivery device includes a gas chamber, a delivery chamber, a gas cell, and a delivery aperture. The gas chamber includes a gas-side rigid portion and a gas-side flexible barrier. The gas-side flexible barrier is sealed to the gas-side rigid portion. The delivery chamber includes a delivery-side rigid portion and a delivery-side flexible barrier. The delivery-side flexible barrier is sealed to the delivery-side rigid portion. The delivery-side flexible barrier is oriented adjacent to the gas-side flexible barrier. The gas cell is coupled to the gas-side rigid portion of the gas chamber. The gas cell increases a gas pressure within the gas chamber to expand the gas-side flexible barrier. Expansion of the gas-side flexible barrier applies a compressive force to the delivery-side flexible barrier. The delivery aperture allows a delivery material to escape from the delivery chamber in response to compression of the delivery-side flexible barrier into the delivery chamber. Other embodiments of the device are also described.

Embodiments of a method are also described. In one embodiment, the method is a method for manufacturing a delivery device. The method includes forming a gas-side rigid portion, forming a gas-side flexible barrier, sealing the gas-side rigid portion to the gas-side flexible barrier to form a gas chamber, forming a delivery-side rigid portion, forming a delivery-side flexible barrier, sealing the delivery-side rigid portion to the delivery-side flexible barrier to form a delivery chamber, sealing the gas chamber to the delivery chamber with the gas-side flexible barrier oriented adjacent to the delivery-side flexible barrier. The method also includes disposing a gas cell in the gas-side rigid portion. The gas cell is in communication with the gas chamber. The method also includes, disposing a delivery aperture in the delivery-side rigid portion. The delivery aperture is in communication with the delivery chamber. Other embodiments of the method are also described.

Embodiments of a system are also described. In one embodiment, the apparatus is a delivery system. The system includes a delivery pump, a dispersion structure, and a control module. The delivery pump operates independent of orientation. The delivery pump includes a gas chamber, a gas cell, and a delivery chamber. The gas chamber includes a gas-side flexible barrier and a gas-side rigid portion. The gas cell is disposed in communication with the gas chamber to increase pressure within the gas chamber and distend the gas-side flexible barrier away from the gas-side rigid portion by generating a gas within the gas chamber. The delivery chamber includes a delivery-side flexible barrier and a delivery-side rigid portion. The delivery chamber is sealed to the gas chamber with the delivery-side flexible barrier oriented directly adjacent to the gas-side flexible barrier. The delivery-side flexible barrier is pressed into the delivery chamber to dispense a delivery material from the delivery chamber in response to distension of the gas-side flexible barrier away from the gas-side rigid portion. The dispersion structure receives the delivery material from the chamber delivery pump. The dispersion structure delivers the delivery material to a delivery site. The control module is coupled to the gas cell. The control module controls an operating parameter of the gas cell. Other embodiments of the system are also described.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

Figure 1:
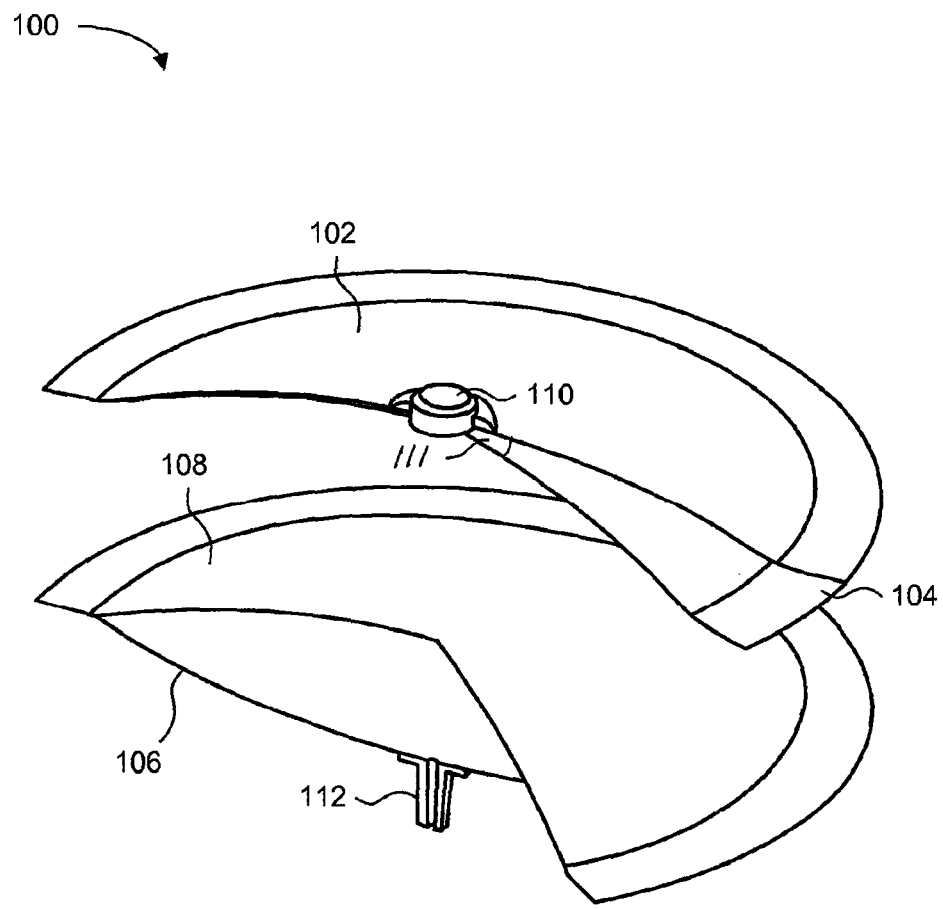
FIG. 1 depicts an exploded cut-away view of one embodiment of a delivery device.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments relate to a gas cell pump. Generally, the embodiments described below are drawn to delivery of a delivery material through mechanical pressure generated by a gas cell. Some embodiments may be useful to deliver medicines, scents, chemical agents, lubricants, saline, or other materials, chemicals, or chemical mixtures. In some embodiments, the pump may deliver the material to a local area. In other embodiments, the pump may deliver the material to a stream of material to yield a certain result at a near or relatively distant site. In another embodiment, the pump delivers the material at a sustained rate. For example, the pump may operate at a relatively slow rate of delivery or at a high rate. In other embodiments, the pump delivers the material at a variable rate.

In some embodiments, the pump can be loaded with a volatile and/or corrosive material for delivery. The pump can be built with materials that are specifically resistant to the particular chemical or agent that will be delivered by the pump. Additionally, some embodiments may incorporate materials that have a low permeability relative to the delivery agent. In this way, some embodiments may be specifically built to deliver a particular substance. Other embodiments may be built to handle a wide range of substances with varying corrosion and permeability characteristics.

In some embodiments, the components of the pump may be sealed together into a single unified piece. In other embodiments, some components may be joined in a manner that allows those components to be removed without damage to the pump or use of complex processes. For example, in some embodiments, the portion containing the delivery material may be removed to replace a spent portion with a new portion. In other embodiments, other portions may be removable.

In some embodiments, the pump is operable in any orientation. In other words, the pump is not sensitive to any particular orientation threshold. For example, the pump may be positioned to dispense a delivery material upwards, downwards, or at any angle in between.

FIG. 1 depicts an exploded cut-away view of one embodiment of a delivery device 100. The illustrated embodiment includes a gas-side rigid portion 102, a gas-side flexible barrier 104, a delivery-side rigid portion 106, a delivery-side flexible barrier 108, a gas cell 110, and a delivery aperture 112. In the depicted embodiment, the gas-side rigid portion 102 is a domed geometry with a flanged edge. The structure of the gas-side rigid portion 102 corresponds with the structure of the gas-side flexible barrier 104. This allows the gas-side rigid portion 102 and the gas-side flexible barrier 104 to match up and form a seal. In other embodiments, the gas-side rigid portion 102 has a different geometry than illustrated. For example, the gas-side rigid portion 102 may have a deeper curvature, it may be cylindrical or spherical, it may have planar portions or be cuboidal, and it may have a concave geometry rather than the convex geometry shown in FIG. 1.

In the illustrated embodiment of FIG. 1, the gas-side rigid portion 102 has a smooth surface. In other embodiments, the gas-side rigid portion 102 has a surface treatment. For example, the surface treatment may include polishing, texturing, added structural elements to increase rigidity or provide some other functionality. In the depicted embodiment, the gas-side rigid portion 102 is made of a relatively rigid material. For example, the gas-side rigid portion 102 may be made of hard plastic, metal, composite, or some other rigid material.

In the depicted embodiment, the gas-side flexible barrier 104 is coupled with the gas-side rigid portion 102. In some embodiments, the gas-side flexible barrier 104 is sealed to the gas-side rigid portion 102. For example, the gas-side flexible barrier 104 and the gas-side rigid portion 102 may be joined by thermal sealing, mechanical sealing, chemical sealing or adhesion, vacuum sealing, or a combination of several forms of sealing or creating a seal.

In some embodiments, the gas-side flexible barrier 104 is a flexible membrane that operates like a diaphragm. As the gas cell 110 generates gas, the gas-side flexible membrane 104 flexes to form a chamber between the gas-side flexible barrier 104 and the gas-side rigid portion 102. As the gas cell 110 continues to generate gas, the gas-side flexible barrier continues to flex to provide additional capacity within the chamber. In some embodiments, the material used for the gas-side flexible barrier 104 may be selected to have a high degree of resistance to reactivity with the gas generated by the gas cell 110. Additionally, the gas-side flexible barrier 104 may be selected to provide a low degree of permeability relative to the gas generated by the gas cell 110. In some embodiments, a material may be selected for both chemical reactivity and permeability. In other embodiments, additional qualities and characteristics may influence material selection for the gas-side flexible barrier 104. Materials which might be used either alone or in combination include acrylonitrile, methyl acrylate copolymer, poly ethylene terephthalate (PET), high density polyethylene (HDPE), also laminates such as biaxial aliphatic polyamides (also known as Nylon), aluminum foil, and low density polyethylene.

In some embodiments, the gas-side flexible barrier 104 is flexible throughout its entirety. In other embodiments, the gas-side flexible barrier 104 includes some rigid or relatively less-flexible portions incorporated within the gas-side flexible barrier 104. In some embodiments, the gas-side flexible barrier 104 has portions with varying degrees of flexibility. For example, the gas-side flexible barrier 104 may have a small rigid portion 111 that prevents the gas-side flexible barrier 104 from contacting the gas cell 110 when the gas-side flexible barrier 104 is fully collapsed against the gas-side rigid portion 102. Other embodiments incorporate other structural elements within the gas-side flexible barrier 104 to provide other functionality.

In some embodiments, the delivery-side rigid portion 106 is similar to the gas-side rigid portion 102. In other embodiments, the delivery-side rigid portion 106 is unique in form and functionality. For example, the delivery-side rigid portion 106 may be formed to improve the flow of delivery material to the delivery aperture 112 or may include a refill interface (not shown). Other functionality and structure may be included in other embodiments. In some embodiments, the delivery-side rigid portion 106 matches the form of the gas-side rigid portion 102 where they meet to facilitate sealing the delivery side (116 of FIG. 3B) and the gas side (114 of FIG. 3B) together. In other embodiments, the delivery-side rigid portion 106 varies in geometry from the gas-side rigid portion 102.

The delivery-side flexible barrier 108 is coupled to the delivery-side rigid portion 106. In some embodiments, the delivery-side flexible barrier 108 is formed of material with a high degree of chemical resistance relative to a delivery material. In other embodiments, the delivery-side flexible barrier 108 also has a low degree of permeability relative to the delivery material. In some embodiments, the delivery-side flexible barrier 108 has a high degree of permeability relative to the gas generated by the gas cell 110. This would allow any stray gas from the gas cell 110 that has collected on the delivery side (116 of FIG. 3B) to escape through the delivery-side flexible barrier 108 without forming a bubble or otherwise affecting the delivery side (116 of FIG. 3B) of the device 100. In some embodiments, similar gas venting functionality is incorporated into the delivery-side rigid portion 106.

In the illustrated embodiment, the gas cell 110 is disposed in the structure of the gas-side rigid portion 102. In some embodiments, the gas cell 110 is disposed in the structure of the gas-side rigid portion 102 by application of a glass bead, silicon bead, cyanoacrylate adhesive or other form of sealant or adhesive material or process. In some embodiments, the gas cell 110 may be located at a remote site and be connected by channels or tubes to direct the gas generated by the gas cell 110 through the gas-side rigid portion 102. The gas cell 110 produces a gas and directs the gas into the area between the gas-side rigid portion 102 and the gas-side flexible barrier 104. The buildup of the gas in this area forces the gas-side flexible barrier 104 to move away from the gas-side rigid portion 102. This provides the driving forces for operation of the device.

In some embodiments, the gas cell 110 is an electrochemical cell. Gas cell technology is taught by Gordon in U.S. Pat. Nos. 5,744,014 and 5,899,381 which are incorporated herein by reference The illustrated embodiment of FIG. 1 includes the delivery aperture 112. In some embodiments, the delivery aperture 112 is a separate structure disposed in the delivery-side rigid portion 106. In other embodiments, the delivery aperture 112 is formed as part of the delivery-side rigid portion 106. The delivery aperture 112 allows a delivery material to be released from the delivery side (116 of FIG. 3B) of the device. In some embodiments, the delivery aperture 112 includes a valve (not shown) to prevent release of the delivery material until a certain pressure threshold or other criteria are reached. In some embodiments, the delivery aperture 112 includes an attachment point to facilitate attachment of a dispersion structure (discussed further below) to disperse the delivery material released through the delivery aperture 112. In some embodiments, the delivery aperture 112 is made of or includes an activator to cause a chemical reaction in the delivery material as it passes through the delivery aperture 112. For example, the delivery aperture 112 may include a heater, a chemical activator, an electrically charged element, or other structure to interact with the delivery material as it passes through the delivery aperture 112. In another embodiment, the delivery aperture 112 physically affects the delivery mode of the delivery material. For example, the delivery aperture 112 may atomize, collimate, stream, spread, accelerate, slow, vary, or modulate the delivery of the delivery material.

Although the delivery device 100 is shown and described with certain components and functionality, other embodiments of the delivery device 100 may include fewer or more components to implement less or more functionality.

Figure 2:
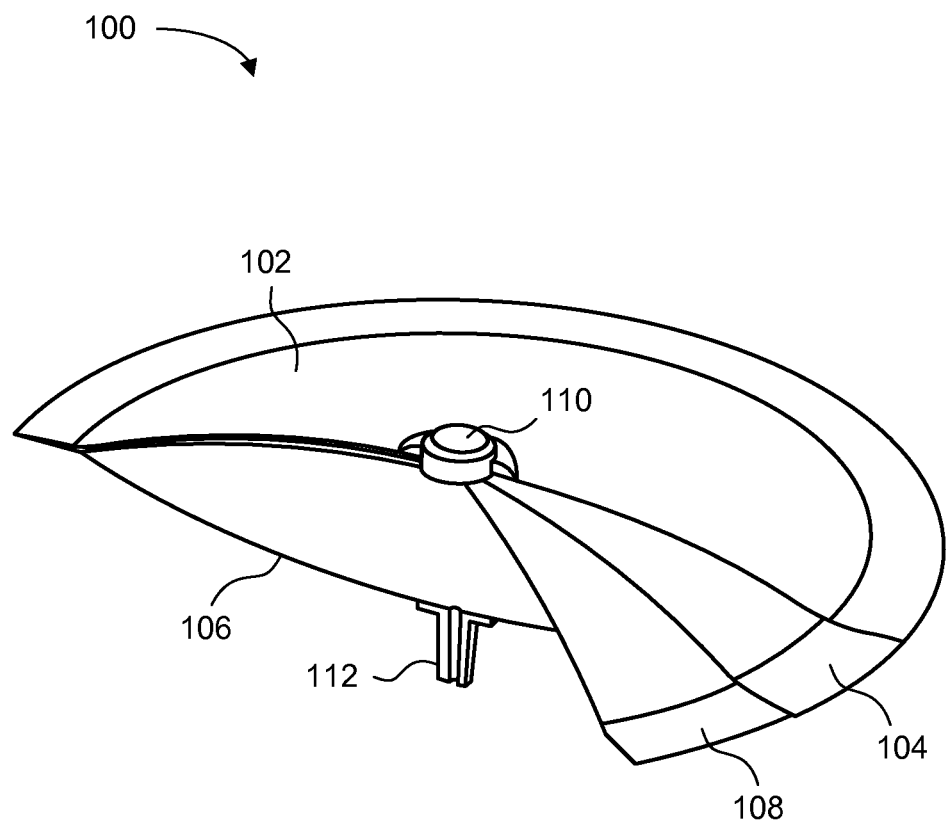
FIG. 2 depicts a cut-away schematic diagram of one embodiment of the delivery device of FIG. 1 with the gas-side flexible barrier fully compressed.

FIG. 2 depicts a cut-away schematic diagram of one embodiment of the delivery device 100 of FIG. 1 with the gas-side flexible barrier 104 fully compressed. The illustrated embodiment of the delivery device 100 includes the gas-side rigid portion 102, the gas-side flexible barrier 104, the delivery-side rigid portion 106, the delivery-side flexible barrier 108, the gas cell 110, and the delivery aperture 112.

In the illustrated embodiment, the delivery side (116 of FIG. 3B) has been loaded with a delivery material so that the delivery-side flexible barrier is extended. This compresses the gas side (114 of FIG. 3B) so that the gas-side flexible barrier 104 conforms to the form of the gas-side rigid portion 102. In the illustrate embodiment of FIG. 2, the gas cell 110 has not begun generating gas and the gas-side flexible barrier 104 is collapsed against the gas-side rigid portion 102. Once the gas cell 110 begins generating gas, the area between the gas-side rigid portion 102 and the gas-side flexible barrier 104 will fill with the gas and the gas-side flexible barrier 104 with begin to compress the delivery-side flexible barrier 108. This will result in increased pressure between the delivery-side flexible barrier 108 and the delivery-side rigid portion 106.

Figure 3A:
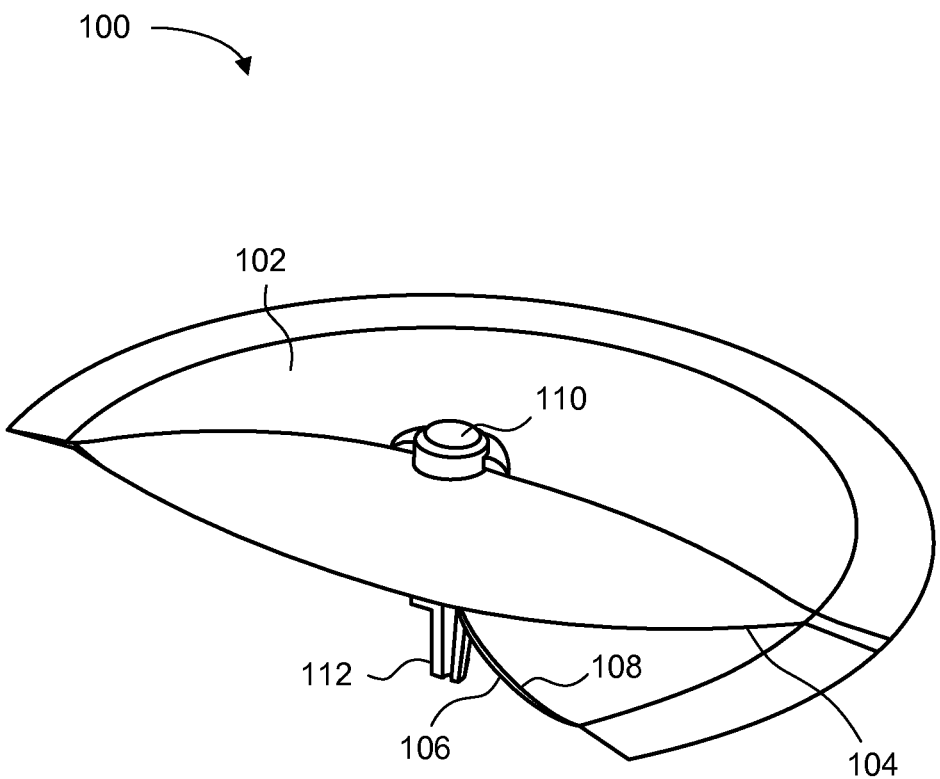
FIG. 3A depicts a cut-away schematic diagram of one embodiment of the delivery device 100 of FIG. 1 with the delivery-side flexible barrier fully compressed.

FIG. 3A depicts a cut-away schematic diagram of one embodiment of the delivery device 100 of FIG. 1 with the delivery-side flexible barrier 108 fully compressed. In the illustrated embodiment, the gas cell 110 has generated enough gas to force the gas-side flexible barrier 104 away from the gas-side rigid portion 102 to compress the delivery-side flexible barrier 108. This has expelled the delivery material through the delivery aperture 112 and collapsed the delivery-side flexible barrier 108 against the delivery-side rigid portion 106.

Figure 3B:
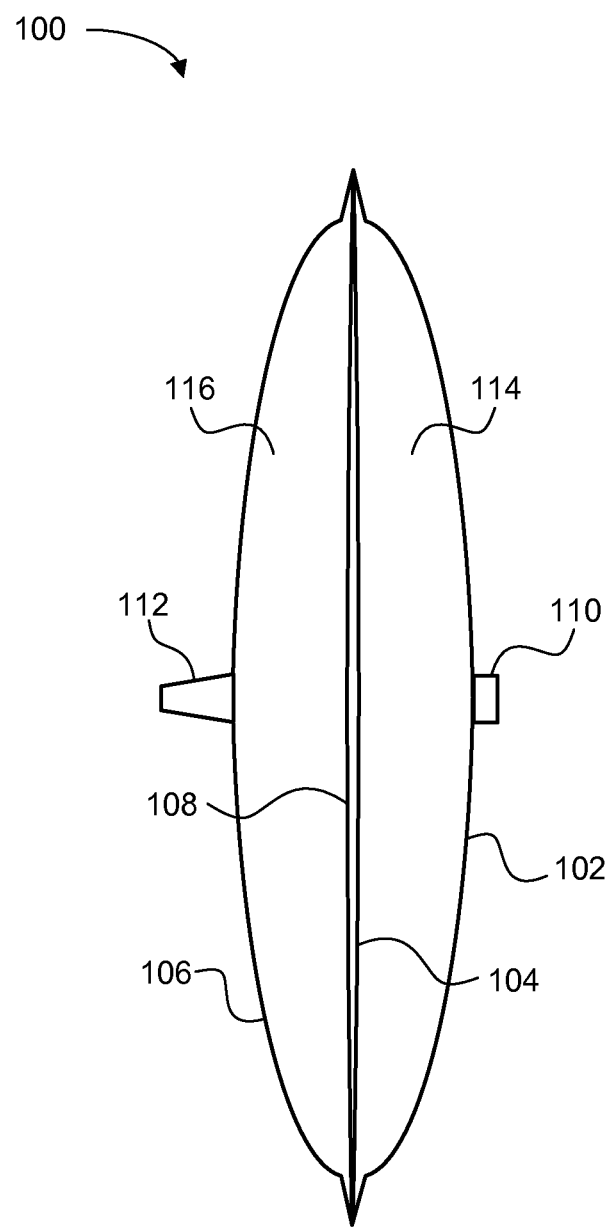
FIG. 3B depicts a schematic diagram of one embodiment of the delivery device of FIG. 1 with the flexible barriers and in neutral position.

FIG. 3B depicts a schematic diagram of one embodiment of the delivery device 100 of FIG. 1 with the flexible barriers 104 and 108 in neutral position. In the illustrated embodiment, the gas-side flexible barrier 104 and the delivery-side flexible barrier 108 are in neutral position. This more readily depicts the gas chamber 114 or gas side 114 of the delivery device 100 as well as the delivery chamber 116 or delivery side 116 of the delivery device 100. In the illustrated embodiment of FIG. 3B, the gas-side flexible barrier 104 and the delivery-side flexible barrier 108 are separated by a small margin. In some embodiments, the relatively small space between the gas-side flexible barrier 104 and the delivery-side flexible barrier 108 is filled with a buffer material to reduce friction and binding between the gas-side flexible barrier 104 and the delivery-side flexible barrier 108. In other embodiments, the gas-side flexible barrier 104 and the delivery-side flexible barrier 108 are in direct contact without separation. In some embodiments, one or both of the gas-side flexible barrier 104 and the delivery-side flexible barrier 108 include surface treatments to reduce friction and substantially prevent binding between the gas-side flexible barrier 104 and the delivery-side flexible barrier 108.

Figure 4:
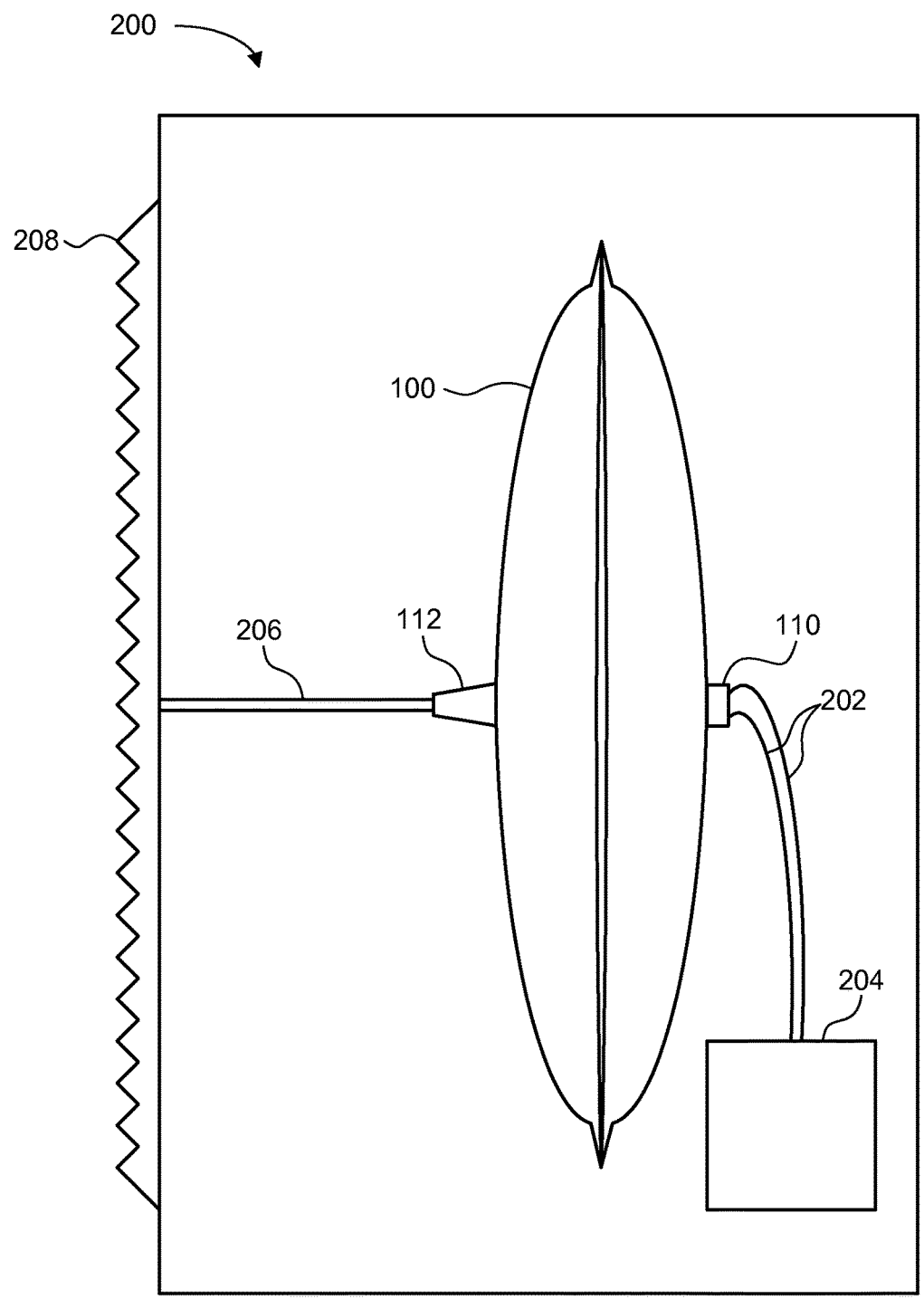
FIG. 4 depicts a schematic diagram of one embodiment of a delivery system.

FIG. 4 depicts a schematic diagram of one embodiment of a delivery system 200. The illustrated embodiment includes a delivery pump 100, a control module 204, leads 202, delivery line 206, and dispersion structure 208. In the illustrated embodiment, the pump 100 includes a gas cell 110 and a delivery aperture 112. In the illustrated embodiment, the pump 100 is in a vertical orientation. In other embodiments, the pump may be oriented horizontally, or at some other angle. In the illustrated embodiment, the gas cell 110 is connected by leads 202 to a control module 204. In some embodiments, the control module 204 includes resistive elements to control the gas cell 110. Other embodiments include other types of electrical or mechanical control systems.

In the illustrated embodiment, the delivery aperture 112 is connected to the delivery line 206. In some embodiments, the delivery line 206 is a tube or channel. The delivery line 206 is connected to the dispersion structure 208 to communicate a delivery material from the delivery aperture 112 of the pump 100 to the dispersion structure 208. In some embodiments, the delivery line 206 is omitted and the delivery aperture 112 is in direct communication with the dispersion structure 208. In some embodiments, the dispersion structure 208 is a molecular dispersion media. For example, the dispersion structure 208 may include gauze, foam, sponge, or other breathable surface area. In another embodiment, the dispersion structure 208 is a spray nozzle. In other embodiments, the dispersion structure 208 is a tube, a needle, a heated element, or other known mechanical, thermal, chemical or other element for delivery of a material to a target location or environment. In another embodiment, the dispersion structure 208 is omitted and the delivery aperture 112 disperses the delivery material from the pump directly out from the delivery system 200. In some embodiments, the pump 100 is implemented within the delivery system 200 to provide certain advantages over conventional technologies. For example, some embodiments of the delivery system 200 implement the pump 100 to eliminate orientation dependencies. For example, the delivery system 200 may be oriented in any direction without suffering leakage or failure in the pump 100. Other embodiments of the delivery system 200 may implement the pump 100 to achieve other advantages.

Although the delivery system 200 is shown and described with certain components and functionality, other embodiments of the delivery system 200 may include fewer or more components to implement less or more functionality.

Figure 5:
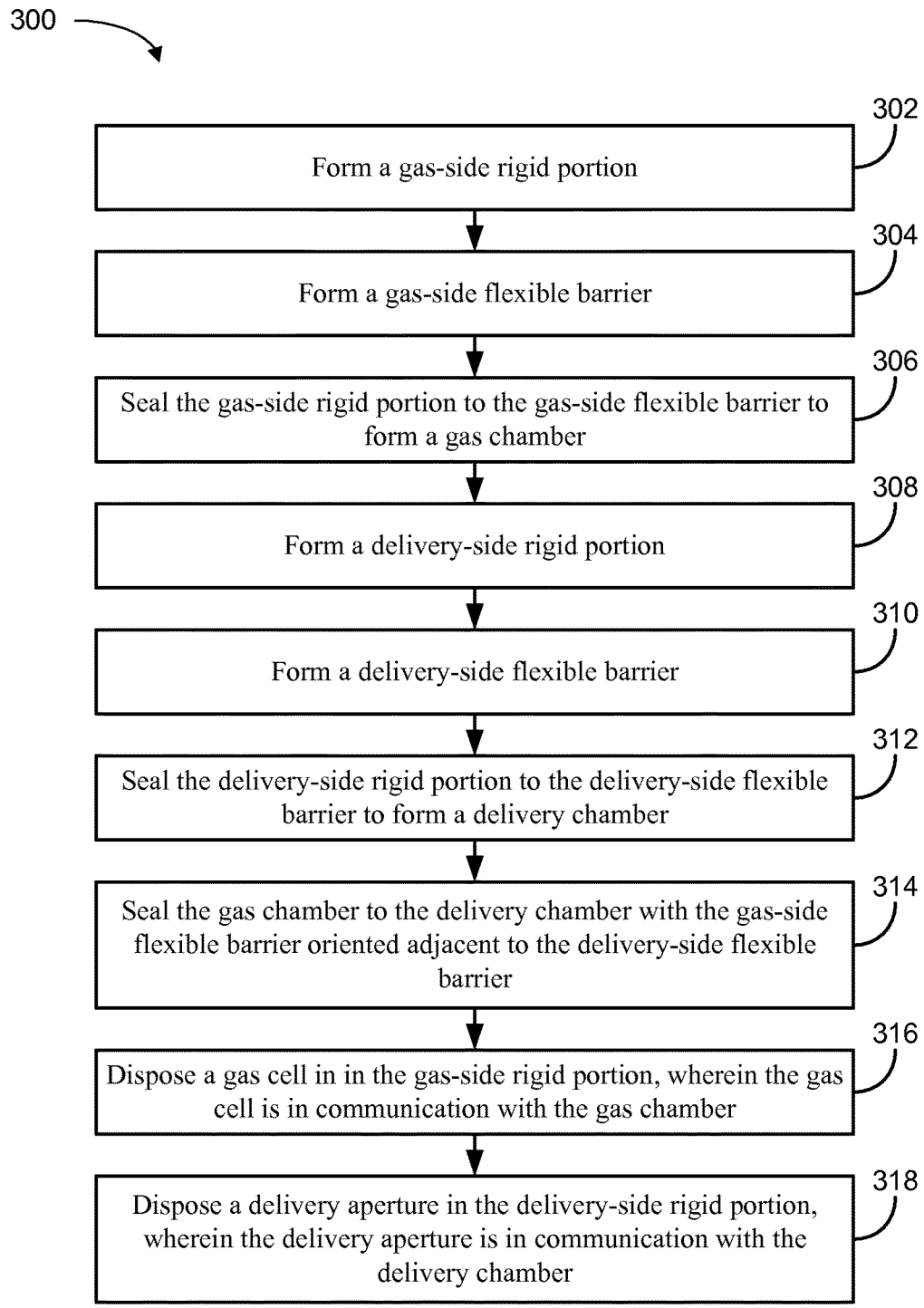
FIG. 5 depicts a block diagram of one embodiment of a method of manufacturing a chamber delivery system.

FIG. 5 depicts a block diagram of one embodiment of a method 300 of manufacturing a chamber delivery system. At block 302, a gas-side rigid portion is formed. At block 304, a gas-side flexible barrier is formed. At block 306, the gas-side rigid portion is sealed to the gas-side flexible barrier to form a gas chamber. At block 308, a delivery-side rigid portion is formed. At block 310, a delivery-side flexible barrier is formed. At block 312, the delivery-side rigid portion is sealed to the delivery-side flexible barrier to form a delivery chamber. At block 314, the gas chamber is sealed to the delivery chamber with the gas-side flexible barrier oriented adjacent to the delivery-side flexible barrier. At block 316, a gas cell is disposed in the gas-side rigid portion. The gas cell is in communication with the gas chamber. At block 318, a delivery aperture is disposed in the delivery-side rigid portion. The delivery aperture is in communication with the delivery chamber.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

What is claimed is:

1. An orientation independent delivery device comprising:
   a gas chamber comprising a gas-side rigid portion and a gas-side flexible barrier element, wherein the gas-side flexible barrier element is permanently sealed, around a first perimeter of the gas chamber, to the gas-side rigid portion such that gas introduced to the gas chamber is confined between the gas-side flexible barrier element and the gas-side rigid portion;
   a delivery chamber comprising a delivery-side rigid portion and a delivery-side flexible barrier element, wherein the delivery-side flexible barrier element is permanently sealed, around a second perimeter of the delivery chamber, to the delivery-side rigid portion such that delivery material introduced to the delivery chamber is confined between the delivery-side flexible barrier element and the delivery-side rigid portion, the delivery-side flexible barrier element being oriented adjacent to, and a distinct element from, the gas-side flexible barrier element;
   a self-powered gas cell coupled to the gas-side rigid portion of the gas chamber, the gas cell to increase a gas pressure within the gas chamber to expand the gas-side flexible barrier element, wherein expansion of the gas-side flexible barrier element applies a compressive force to the delivery-side flexible barrier element; and
   a delivery aperture to allow a delivery material to escape from the delivery chamber in response to deflection of the delivery-side flexible barrier element in a direction toward the delivery-side rigid portion, wherein:
   the gas-side rigid portion and the delivery-side rigid portion cooperate to define a constant volume during storage and use of the delivery device;
   the gas chamber is permanently sealed to the delivery chamber to form a single unified piece; and the gas-side flexible barrier element has an outer surface that is in continuous direct contact with the delivery-side flexible barrier element without separation.

2. The device of claim 1, wherein the gas-side flexible barrier element comprises a material with a permeation coefficient of between 7.4 and 0.002 $cm^2/s$-Pa for gas generated by the gas cell at standard temperature and pressure conditions.

3. The device of claim 1, wherein the gas-side flexible barrier element comprises a material that is non-reactive with gas generated by the gas cell.

4. The device of claim 1, wherein the delivery-side flexible barrier element comprises a material with a delivery material permeation coefficient of between 7.4 and 0.002 $cm^2/s$-Pa for gas generated by the gas cell at standard temperature and pressure conditions.

5. The device of claim 1, wherein the delivery-side flexible barrier element comprises a material that is non-reactive with the delivery material.

6. The device of claim 1, wherein the seal between the gas chamber and the delivery chamber extends completely around the delivery chamber.

7. The device of claim 1, further comprising a dispersion structure coupled to the delivery aperture, the dispersion structure comprising molecular dispersion media with a breathable surface area to facilitate delivery of the delivery material to a delivery location.

8. The device of claim 1, wherein the gas cell comprises a galvanic cell.

9. The device of claim 8, wherein the galvanic cell generates hydrogen gas.

10. A delivery system comprising:

a delivery pump, wherein the delivery pump operates independent of orientation, the delivery pump comprising:

a gas chamber comprising a gas-side flexible barrier membrane and a gas-side rigid portion, the gas-side flexible barrier membrane being permanently sealed, around a perimeter of the gas chamber, to the gas-side rigid portion such that gas introduced to the gas chamber is confined between the gas-side flexible barrier membrane and the gas-side rigid portion;

a self-powered gas cell disposed in communication with the gas chamber to increase pressure within the gas chamber and distend the gas-side flexible barrier membrane away from the gas-side rigid portion by generating a gas within the gas chamber between said gas-side rigid portion and said gas-side flexible barrier membrane, gas in the gas chamber being in contact with the gas-side rigid portion and with the gas-side flexible barrier membrane;

a delivery chamber comprising a volume defined between a delivery-side flexible barrier membrane and a delivery-side rigid portion, the delivery-side flexible barrier membrane being permanently sealed, around a perimeter of the delivery chamber, to the delivery-side rigid portion such that delivery material introduced to the delivery chamber is confined between the delivery-side flexible barrier membrane and the delivery-side rigid portion, wherein the delivery chamber is coupled to the gas chamber to form a single unified piece with the delivery-side flexible barrier membrane being oriented directly adjacent to the gas-side flexible barrier membrane, wherein the gas-side flexible barrier element has an outer surface that is in continuous direct contact with the delivery-side flexible barrier element without separation, wherein the delivery-side flexible barrier membrane is configured to be pressed into the delivery chamber to dispense a delivery material from the delivery chamber in response to distension of the gas-side flexible barrier membrane away from the gas-side rigid portion, wherein the gas-side rigid portion and the delivery-side rigid portion together define a constant volume during storage and use of the delivery system;

a dispersion structure to receive the delivery material from the delivery pump, wherein the dispersion structure comprises molecular dispersion media having a breathable surface area to deliver the delivery material to a delivery site; and a control module coupled to the gas cell of the delivery pump, the control module to control an operating parameter of the gas cell.

11. The system of claim 10, wherein the gas cell comprises a hydrogen generating galvanic cell.

12. The system of claim 10, wherein the gas-side flexible barrier membrane comprises a material that is non-reactive relative to the gas and having a gas permeation coefficient between 7.4 and 0.002 $cm^2/s$-Pa at standard temperature and pressure conditions.

13. The system of claim 10, wherein the delivery-side flexible barrier membrane comprises a material of relatively low delivery material permeability and reactivity compared to the delivery material.

14. The device of claim 1, wherein the gas-side rigid portion and the delivery-side rigid portion are affixed together to place the first perimeter in agreement with the second perimeter.

* * * * *